United States Patent [19]

Martinez et al.

[11] Patent Number: 4,776,843
[45] Date of Patent: Oct. 11, 1988

[54] BLOOD ACCESS SYSTEMS

[75] Inventors: Felix J. Martinez; Louis C. Cosentino, both of Plymouth; Bruce P. Amiot, St. Louis Park; Raymond F. Cracauer, Minneapolis; Larry E. Fuller, Minnetonka, all of Minn.

[73] Assignee: Minntech Corporation, Minneapolis, Minn.

[21] Appl. No.: 209,058

[22] Filed: Nov. 21, 1980

[51] Int. Cl.$^4$ .......................................... A61M 37/00
[52] U.S. Cl. ...................................... 604/86; 604/201
[58] Field of Search ............ 128/214.6, 213 A, 213 R, 128/764, 763, 767; 604/169, 86, 88, 201, 165, 167

[56] References Cited

U.S. PATENT DOCUMENTS

| | | | |
|---|---|---|---|
| 3,402,710 | 9/1968 | Paleschuck | 128/1 |
| 3,502,097 | 3/1970 | Muller | 128/214.6 |
| 3,663,965 | 5/1972 | Lee et al. | 3/1 |
| 3,765,032 | 10/1973 | Palma | 3/1 |
| 3,783,868 | 1/1974 | Bokros | 3/1 |
| 3,977,400 | 8/1976 | Moorehead | 604/169 |
| 4,015,601 | 4/1977 | Bokros et al. | 128/214 R |
| 4,092,983 | 6/1978 | Slivenko | 128/214 R |
| 4,108,173 | 8/1978 | Slivenko et al. | 128/214 R |
| 4,108,174 | 8/1978 | Slivenko | 128/214 R |
| 4,121,585 | 10/1978 | Becker, Jr. | 128/214.6 |
| 4,164,221 | 8/1979 | Bentley et al. | 128/214 R |

FOREIGN PATENT DOCUMENTS

| | | |
|---|---|---|
| 2049513 | 3/1971 | France ................ 128/214.6 |
| 2000684 | 1/1979 | United Kingdom . |
| 2056282 | 3/1981 | United Kingdom . |

OTHER PUBLICATIONS

Proceedings of Seventh Annual Contractors' Conference of the Artificial Kidney Program of the National Institute of Arthritis, Metabolism and Digestive Diseases, pp. 160–161 (1974).
H. Tenckhoff, Chronic Peritoneal Dialysis Manual, FIGS. I–VII.
Brochure, "Pyrolite (R) Carbon Coating for Prosthetic Devices", General Atomic Corp. (1974).
"Reciprocating Peritoneal Dialysis with a Subcutaneous Peritoneal Catheter", Dialysis and Transplantation, vol. 7, pp. 834–835 and 838 (Aug. 1978).
Mpls, Medical Research Foundation, Mpls., MN, "Implantable Subcutaneous Blood Access with a Percutaneous, Puncturable Septum", excerpt from the 11th Annual Contractors' Conference, Jan. 16–18, 1978.
Mpls. Medical Research Foundation, Mpls., MN, "Evaluation of Implantable Subcutaneous Carbon Blood Access Device with Percutaneous Spigot Valve", excerpt from the 11th. Annual Contractors' Conference of Artificial Kidney Program, etc., Jan. 16–18, 1978.

Primary Examiner—Barry S. Richman
Assistant Examiner—T. J. Wallen
Attorney, Agent, or Firm—Vidas & Arrett

[57] ABSTRACT

Improvements and accessories for a septum closed T-shaped blood access device adapted for implantation into a patient. The implantable device has a stem portion extending above the skin of the patient and defining a septum closed opening into the device. The improvements include an improved septum having a groove in the side thereof encircling the septum and an elastomeric ring carried within the side groove, an improved needle assembly which provides access to the circulatory system through the septum, and a flexible cap for sealing the stem of the implantable device from the outside atmosphere which may be fitted in place or removed without the necessity of specialized tools.

8 Claims, 7 Drawing Sheets

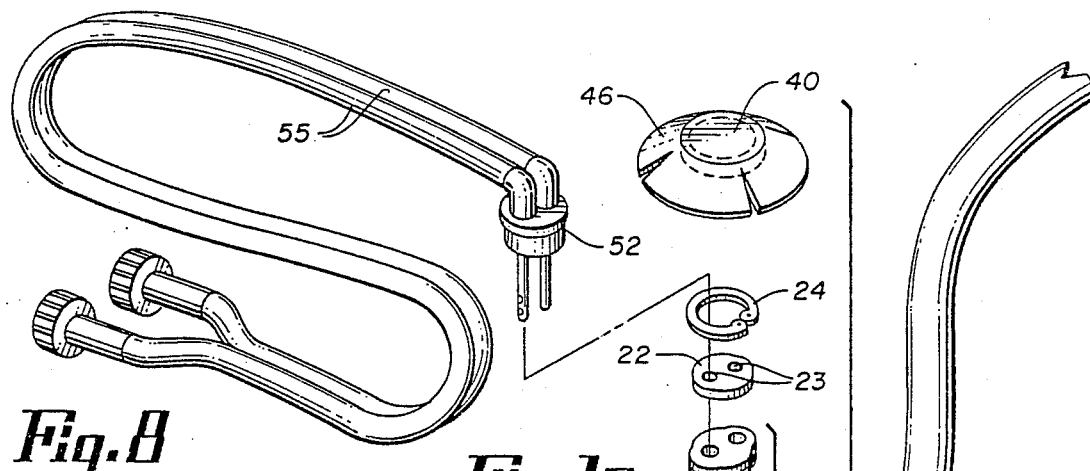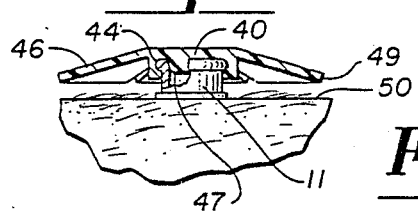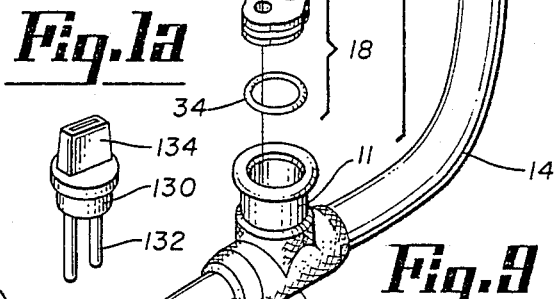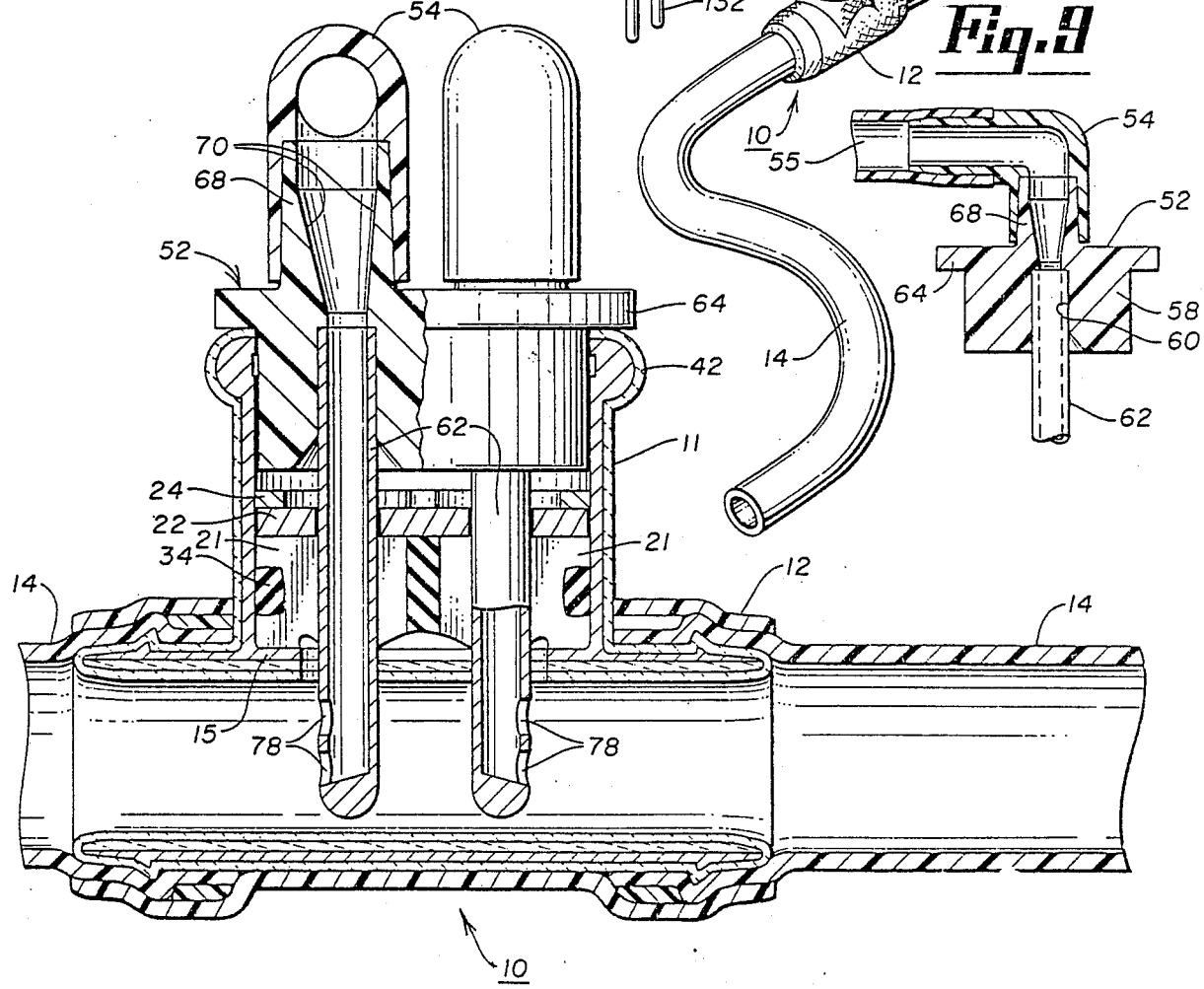

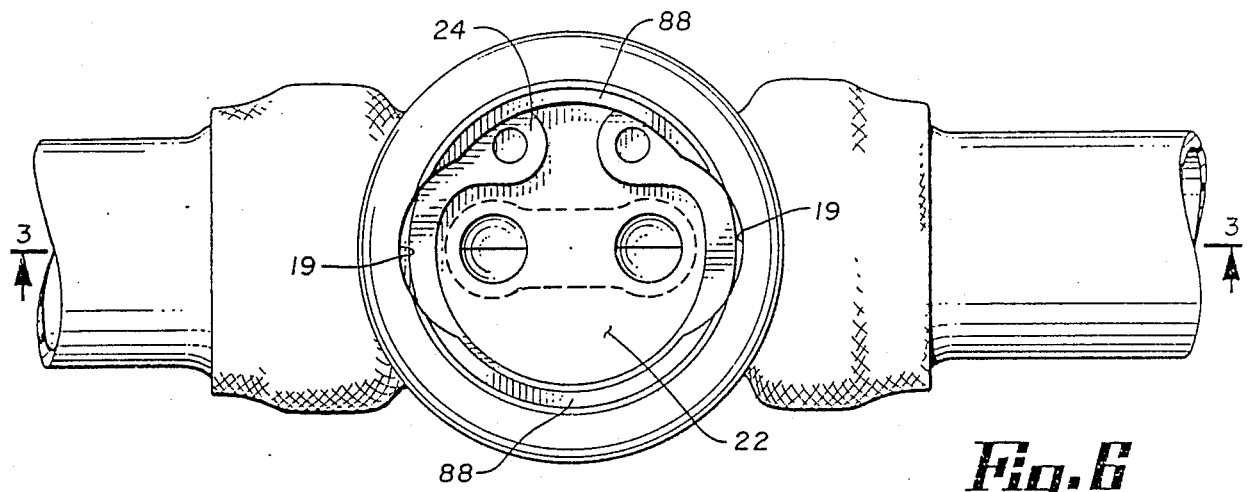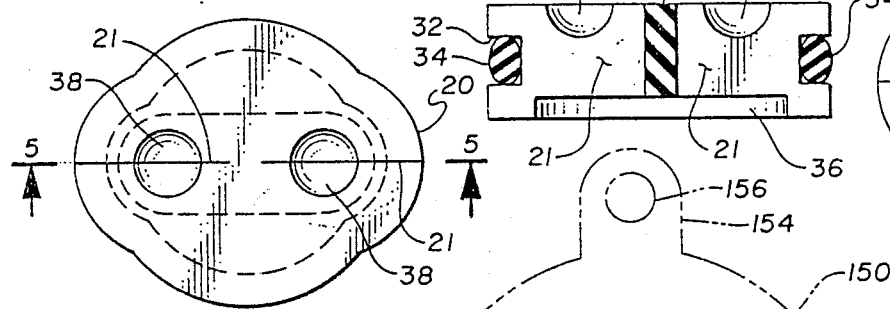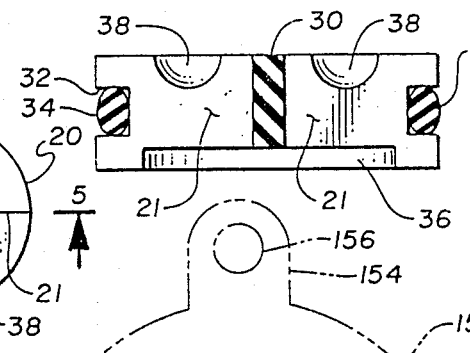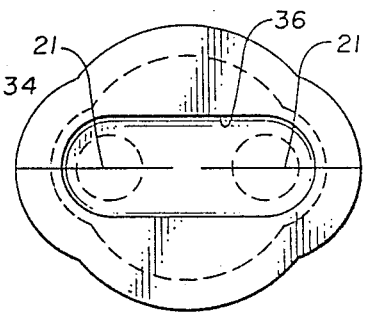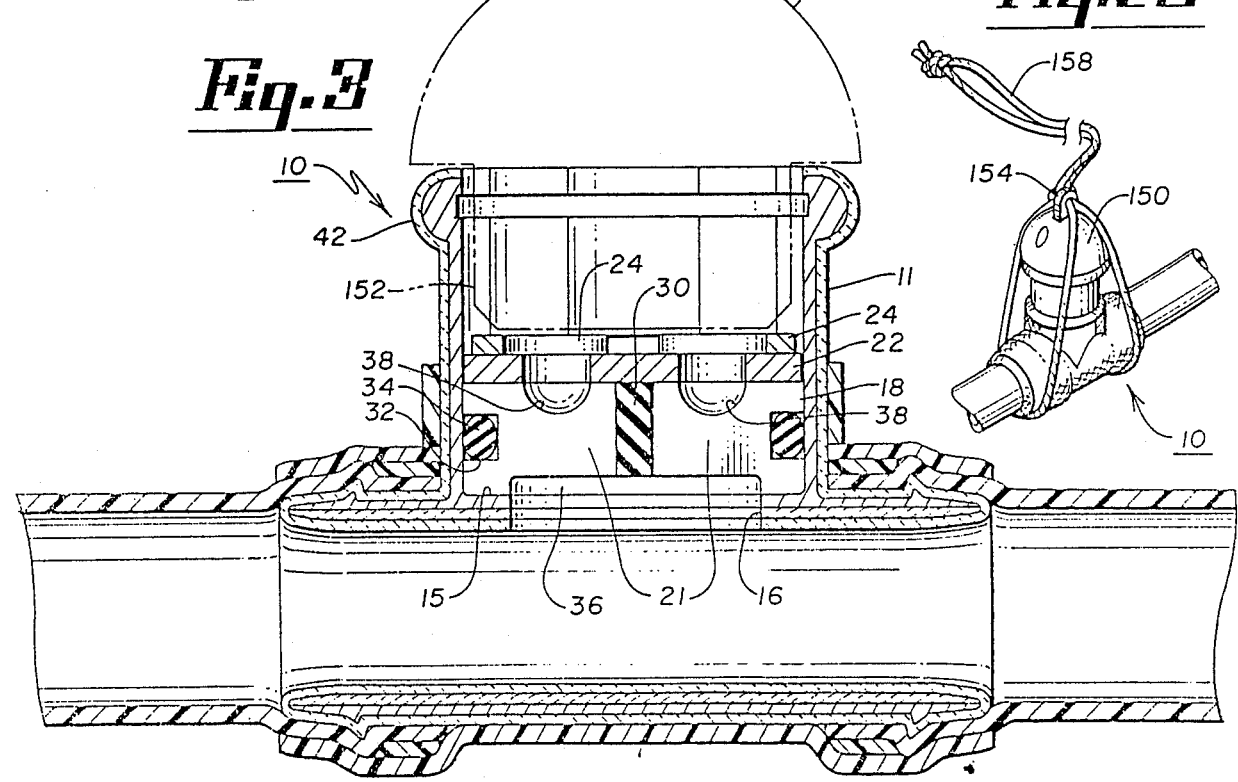

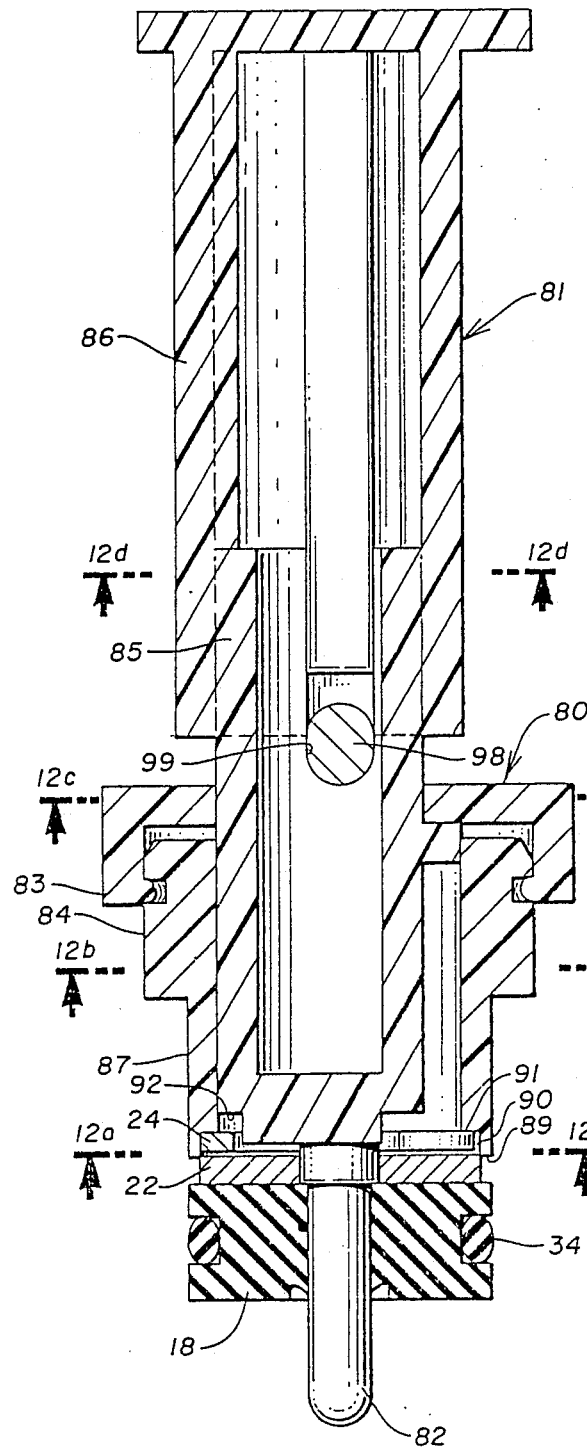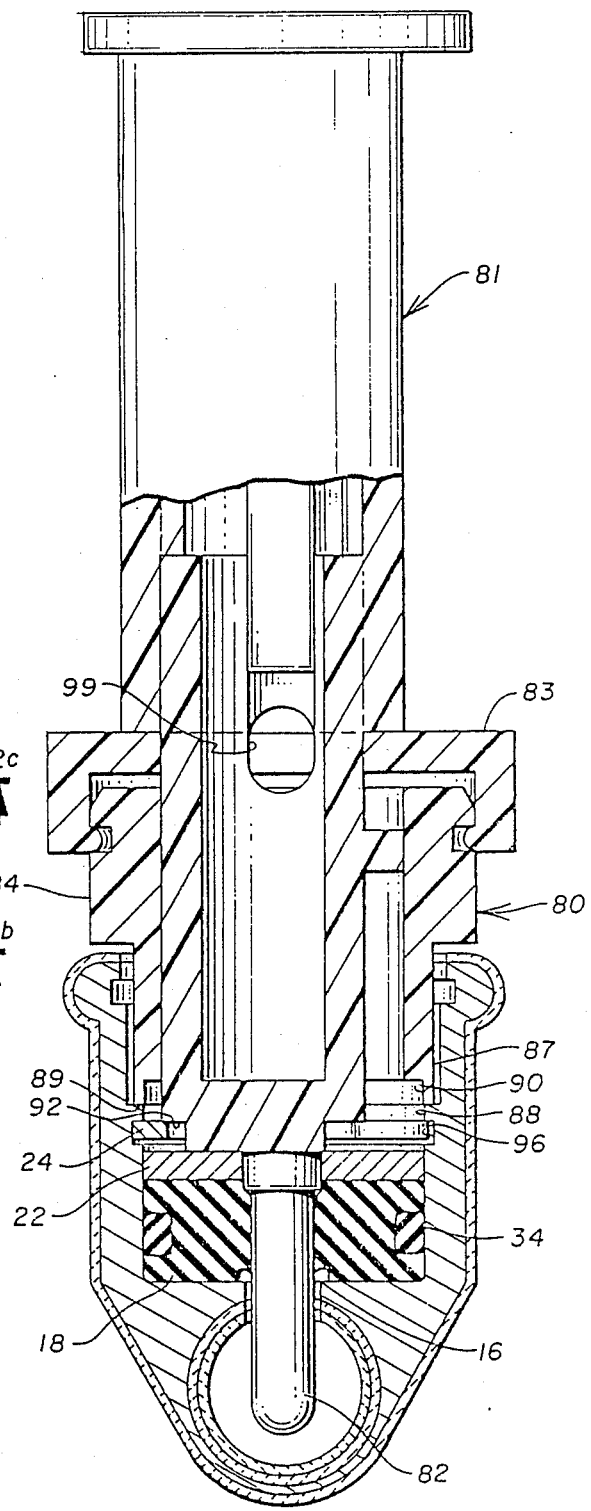

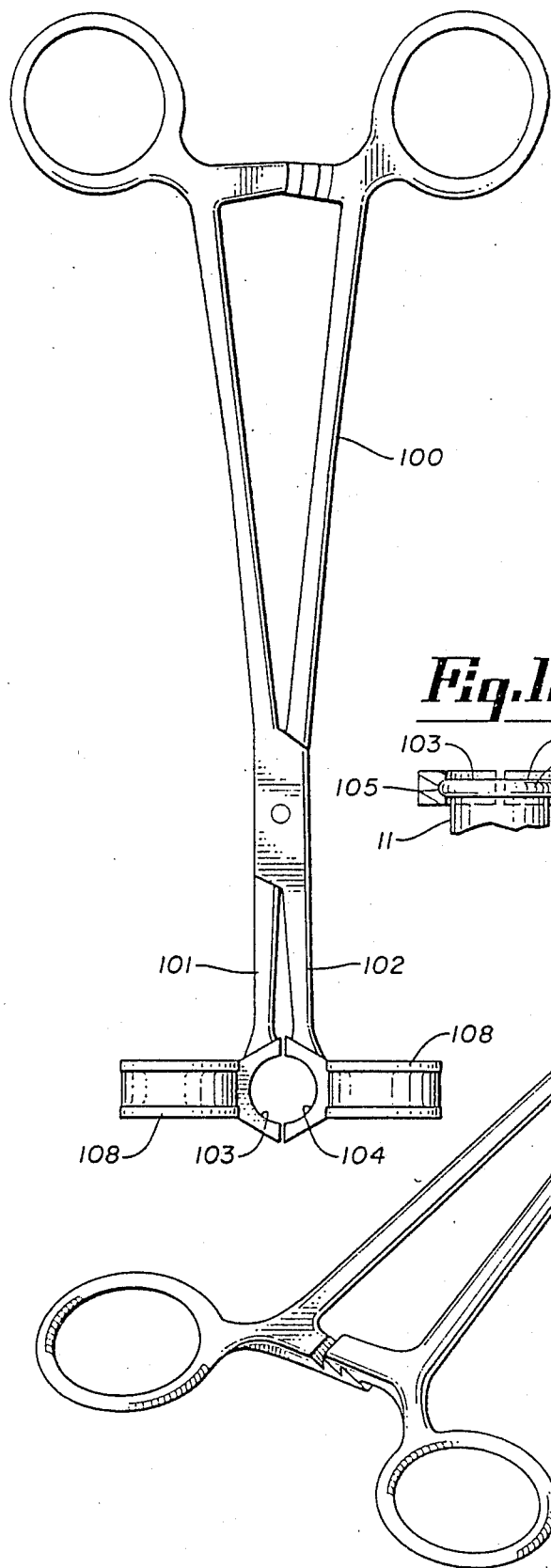
Fig.14
Fig.15
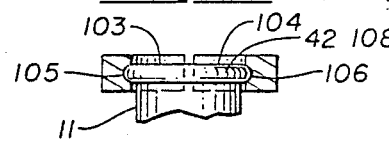
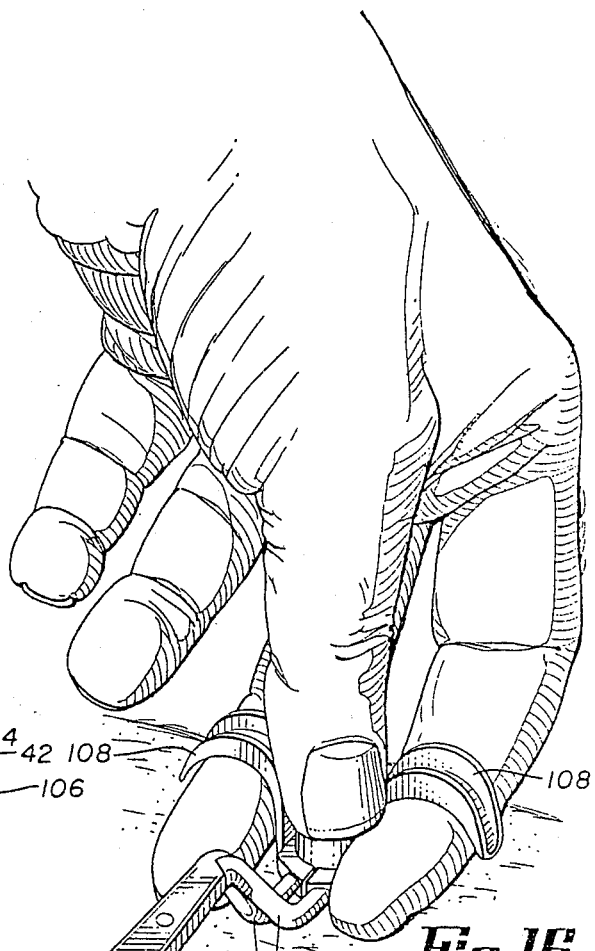
Fig.18
Fig.16
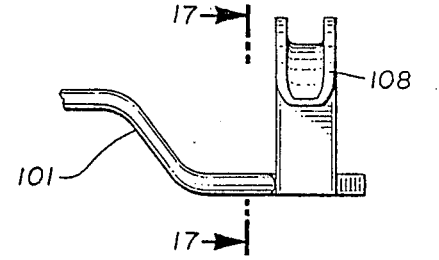
Fig.17
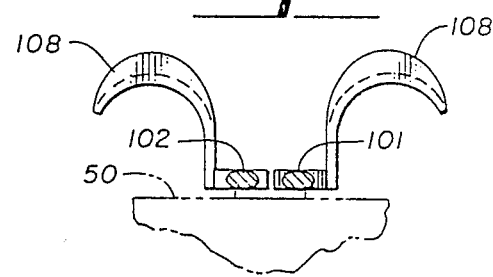

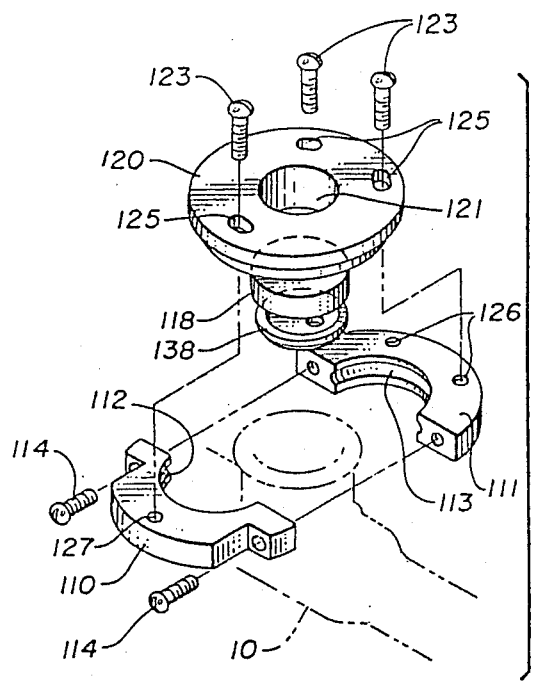
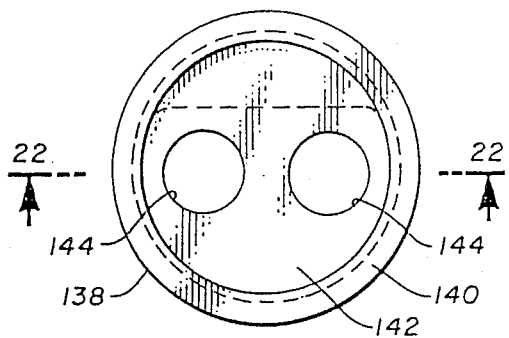
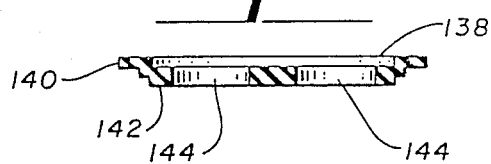
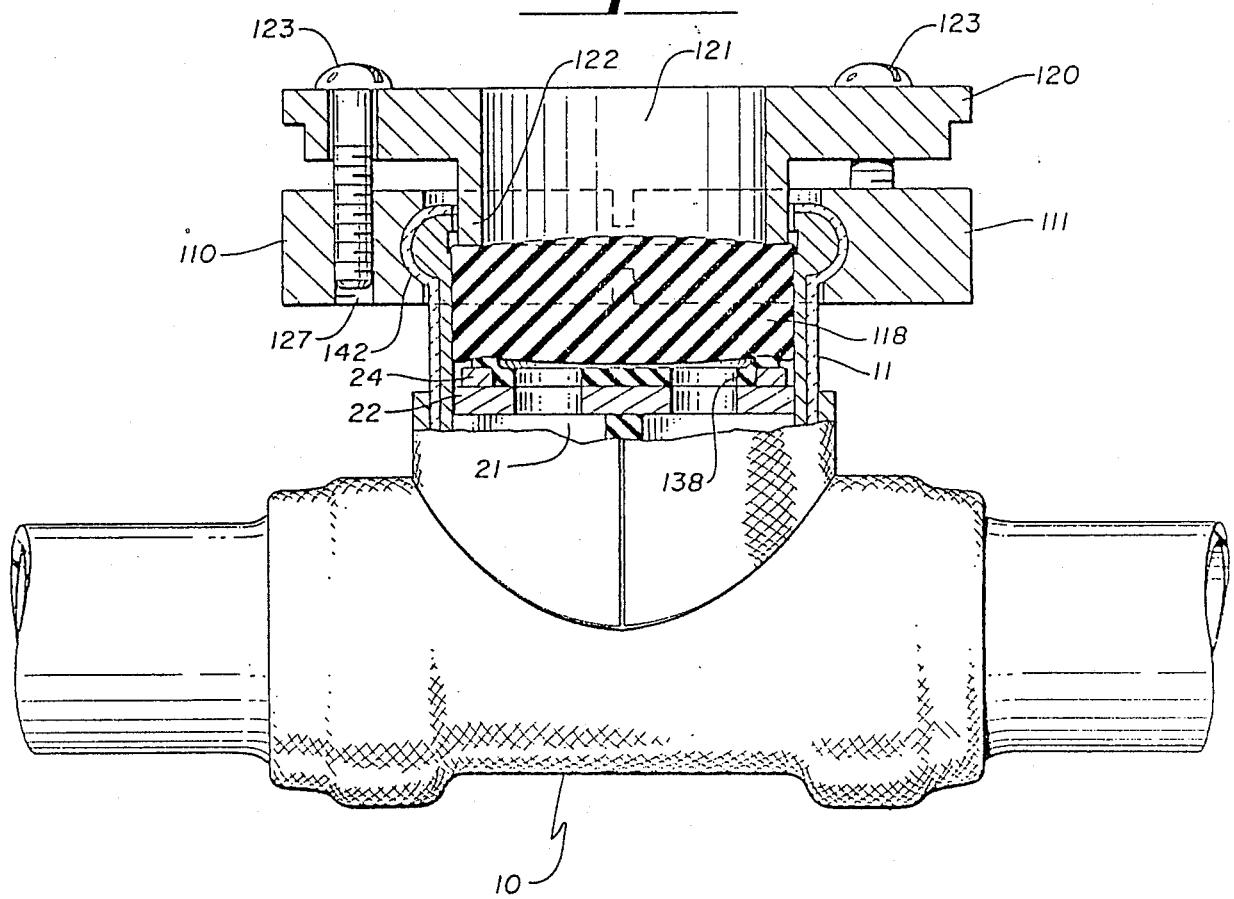

BLOOD ACCESS SYSTEMS

This application relates to improvements in, and accessories for, implantable septum closed blood access devices of the type disclosed in copending application Ser. No. 138,579, filed Apr. 8, 1980 now abandoned, the disclosure of which is incorporated herein by reference.

Various approaches to implanted blood access devices are known; however, none of these have been entirely satisfactory. Shunt techniques have problems of infection, clotting and erosion. The arteriovenous fistula has some advantages over shunts, but there is a need for recurring needle puncture and there are still infection problems as well as other disadvantages.

It is also known to provide implanted blood access devices wherein access to the circulatory system is accomplished by means of a percutaneous spigot valve.

In copending application Ser. No. 138,579, there is disclosed an implantable generally tubular T-shaped structure in which the stem of the T is constructed and arranged to cooperate with a needle structure that penetrates a septum seal means at the junction of the stem of the T with the balance of the T structure. By reason of the structure of the invention, the interior stemmed portion of the T can be rinsed clean and sterilized between each use without elaborate procedures, thus minimizing the likelihood of infection as a result of access to the circulatory system. The invention thus provides an implantable blood access device which may be semi-permanently installed into the circulatory system and used repeatedly. This invention also has a low profile body external portion which minimizes the possible catching of clothing and the like on the external portion.

Further features of the invention of copending application Ser. No. 138,579 include a specialized septum construction, a cooperating needle carrier structure and a cap which seals the flanged edge of the external T-stem.

BRIEF DESCRIPTION OF THE INVENTION

This application discloses improvements in the septum configuration, the needle assembly and the external cap for blood access devices of the type disclosed in application Ser. No. 138,579. Further improvements are specialized tools designed to facilitate placement or replacement of the septum, a back-up septum system which can seal the device while still permitting continued use thereof until assistance can be obtained in replacing a failing septum and an implant cap which is used to protect the interior of the device during implantation thereof.

The new septum configuration has, in the preferred embodiment, two slits running in opposite directions from near the center to the side of the septum, nearly dividing it in half. The side of the septum is recessed in a grooved portion thereof. A ring surrounding the septum and carried within the recess thereof holds the septum together and maintains the slit edges together in sealed relationship by applying a radial force on the septum. Recesses on the top and bottom surface of the septum surrounding the needle penetration points are also provided. This configuration provides improved service life of the septum, especially for silicone base elastomers.

The improved needle assembly presents a right angle profile which makes insertion of the needle pair into the device easier. Tubing connections to the needle carrier are substantially parallel rather than approaching from divergent directions, thereby decreasing likelihood of patient or assistant entanglement with the tubing. Channeling within the carrier between the needles and the tubing connectors permits closer spacing of the needles than that of the tubing connectors. This in turn allows a smaller T-stem for the implanted blood access device of which the needle carrier cooperates. The needles of the assembly have a plurality of side holes on the lower ends thereof, one above another, the total cross-sectional area of which is greater than or equal to the internal diameter of the needles. The plurality of holes maintains flow rate through the needles while reducing likelihood of paring of septum material as the needles pass through the septum.

The cap for the external T-stem protects the interior of the stem from contamination and provides a means whereby an antiseptic may be included in the cavity between the septum and the cap to maintain the sterility of the unit between usage. Whereas the cap structure disclosed in the previous application required a retaining ring to securely hold the cap on the stem, the improved cap is held in place without the necessity of the retaining ring. This is accomplished by making the cap of a flexible material and by providing the interior side surface of the cap with a groove having a slightly smaller diameter than that of the flanged edge of the T-stem. A centrally located protrusion extending downward from the cap assists in maintaining alignment thereof on the T-stem. The cap may be fitted in place or removed without tools making servicing of the unit easier. Slits in the flared edge of the cap improve air circulation under the flared edge of the cap and reduce pressure against the skin if the cap edges come in contact therewith.

Another improvement in the blood access device of application Ser. No. 138,579 is a septum loading tool. In the device of the previous application, it was contemplated that the septum pressure plate and retaining ring would be inserted individually. Insertion of the retaining ring required use of a specially adapted forceps for crimping the ring as it was inserted. This piecemeal assembly procedure created problems because of the time required to insert the septum assembly and because significant patient blood loss occurred during the assembly operation. The blood loss also obstructed the view of the doctor or technician. The loading tool of the present invention is a simple device which holds all three sealing elements. These elements are rapidly and simultaneously inserted in the T-stem by insertion of the tool into the stem and depression of a plunger by the thumb. The simplicity of the device permits factory preassembly and packaging of a disposable loaded tool containing the retaining ring, pressure plate and septum in sterile condition.

A second tool is a specially designed forceps for clamping on the lip of the T-stem while inserting or removing the sealing elements therein. The clamp has finger hooks on either side thereof which permits counter pressure to be applied to the stem as the septum loading tool or forceps push down on the device. The result is less danger of trauma to tissue surrounding the implanted blood access device and stabilization of the device, facilitating placement or replacement of the septum assembly. When used in combination with the septum insertion tool of the present invention, this forceps clamp significantly increases the speed with which a septum may be replaced, thereby limiting blood loss from dialysis patients who typically have low hemoglobin levels.

The back-up septum system of the present invention may be used to temporarily seal the blood access device of application Ser. No. 138,579 while still allowing access to the circulatory system when the primary system has begun to fail. Although the septums of the present invention have especially good sealing characteristics after repeated punctures, lifetimes do vary and it is conceivable that on occasion a septum may begin to leak before it has been replaced. A further improvement in the device of Ser. No. 138,579, therefore, is a clamp which may be used with a second or "back-up" septum placed in the cavity between the septum retaining ring and the top of the implanted T-stem. The clamp holds the back-up septum in place and deforms it in such a way as to assure that the septum seals around the interior surfaces of the T-stem thereby sealing the device until the leaking primary septum can be replaced. The back-up septum may be provided with needle openings therethrough so as to allow continued access to the blood stream.

The final device is a hemispherical cap which is used to cover the T-stem cavity of the device of copending application Ser. No. 138,579 during implantation thereof. A tab defining a hole therethrough is located on the top of the cap. Suture material wound about the T and passed through the hole in the cap tab is used to pull the device stem up through an opening in the skin.

BRIEF DESCRIPTION OF THE DRAWINGS

FIG. 1 is an exploded pictorial view of a T-shaped device in accordance with the device of application Ser. No. 138,579 and including the improved septum cap member and needle carrier of the present disclosure.

FIG. 1a is a pictorial view of an obturator for use with the septums of the present disclosure.

FIG. 2 is a plan top view of the implantable T-shaped assembly with the improved septum included therein.

FIG. 3 is a side elevational view partly in section as taken along the lines 3—3 of FIG. 2 with an implant cap shown in phantom.

FIG. 4 is a plan view of the top side of the septum of the present disclosure.

FIG. 5 is a section view along the lines 5—5 of FIG. 4.

FIG. 6 is a plan view of the bottom interior facing side of the septum of the present disclosure.

FIG. 7 is a sectional view of the implantable blood access device with the improved needle assembly in operative engagement with the improved septum of the present disclosure.

FIG. 8 is a side elevational view partly in section of the implanted blood access device and improved cap structure.

FIG. 9 is a side elevational view partly in section of the improved needle assembly of the present disclosure.

FIG. 11 is a sectional view of the septum loading tool taken along the line 11—11 of FIG. 10.

FIG. 13 is a view of the septum loader as in FIG. 11, but with the loader inserted into the stem of the blood access device and the plunger depressed.

FIG. 14 is a top plan view of the forceps clamp of the present disclosure.

FIG. 15 is a sectional view of the ends of the forceps clamp with portions removed showing the clamp in engagement with the upper flange of the blood access device stem.

FIG. 16 is a side plan view of the end of the forceps clamp.

FIG. 17 is a view of the clamp taken along line 17—17 of FIG. 16.

FIG. 18 is a pictorial view of the clamp as it is held in use.

FIG. 19 is an exploded pictorial view of the back-up septum system of the present invention with the implantable blood access device shown in phantom.

FIG. 20 is a side plan view partly in section of the back-up septum, spacer and clamp in operative engagement with a T-shaped blood access device as disclosed in application Ser. No. 138,579.

FIG. 21 is a top plan view of the spacer member for the back-up septum system.

FIG. 22 is a sectional elevation view of the spaced member taken along lines 22—22 of FIG. 21.

FIG. 23 is a pictorial view of the blood access device of application Ser. No. 138,579 showing the implant cap thereon and suture winding thereabout for implantation in the body.

DETAILED DESCRIPTION OF THE INVENTION

Figure 12A:
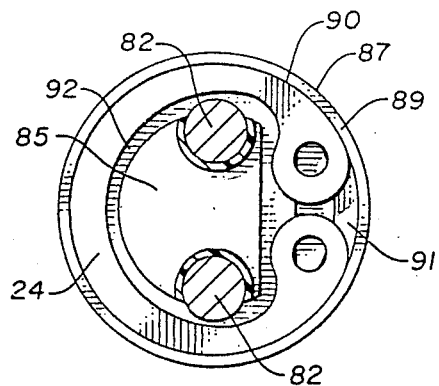
FIGS. 12a, 12b, 12c and 12d are sectional views of the loading tool taken along the lines 12a—12a 12b—12b, 12c—12c and 12d—12d, respectively, of FIG. 11.
Figure 12B:
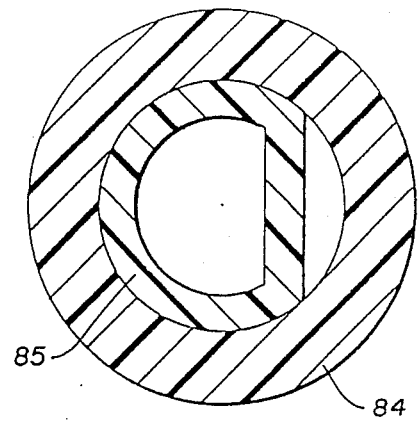
Figure 12C:
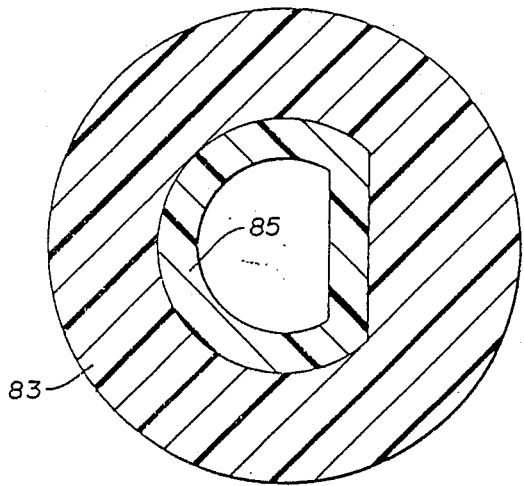
Figure 12D:
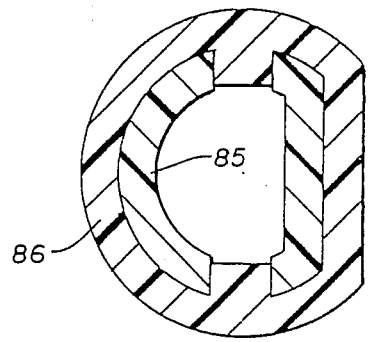
Figure 10:
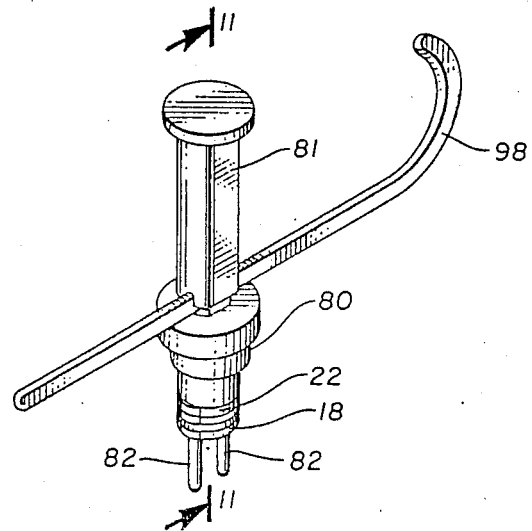
FIG. 10 is a pictorial view of septum loading tool of the present disclosure.

Referring to the drawings, there will be seen in FIG. 1 a blood access device similar to that shown in application Ser. No. 138,579, which includes a T-shaped unitary tubular body generally designated 10 having a stem portion 11 and a straight tube portion 12. Body 10 is formed of a unitary body of a biologically compatible material such as titanium. At least the external surfaces of body 10 may be coated with a continuous layer of pyrolytic carbon to enhance biocompatibility. Expanded tetrafluoroethylene tubes 14 are shown joined to the ends of tube portion 12 by slipping over these ends. The expanded tetrafluoroethylene slipped over the ends of 12 may be provided as an intermediary for joining blood vessels to the assembly 10.

As can best be seen in FIGS. 3 and 7, body 10 is formed with an external extension 15 which substantially provides a separation of the internal chamber of T-shaped member 11 from the cavity of portion 12 except for the opening 16. Member 15 provides a support surface for an improved elastomeric septum member 18 through which a needle or needle pair may gain access to the bloodstream. Member 18 has a broadly elliptical configuration. As can be seen in FIG. 2, stem 11 has a generally round opening. However, there are provided along the axis of tube 12 oppositely disposed protrusions 19 so that the stem opening has an internal shape which conforms generally to the ends 20 of septum 18 for indexing purposes.

Overlying septum 18 is a pressure plate 22 of titanium or other substantially biologically compatible material which defines openings 23 which are spaced to conform in position to slits 21 in the septum and opening 16 in the T-stem. Pressure plate 22 is in turn locked into engagement with septum 18 by a spring retaining ring 24.

Other parts of the tubular blood access device are more fully described in application Ser. No. 138,579.

Improved Septum

It is desirable that septum 18 have a configuration that will allow a maximum number of needle penetrations without leakage through the needle passage. Whereas the septum configuration of application Ser. No. 138,579, which included a precut three-directional star-shaped needle opening and concave septum edges, provided reasonable performance with a natural rubber septum, silicone based elastomeric septums having such a configuration typically begin leaking after 10 or less penetrations. Silicone elastomers, however, have been found to be preferred over natural rubber for septums of the present invention because natural rubber deteriorates upon exposure to betadine (iodine polyvinyl-pyrolidone complex) antiseptic which is used to sterilize the cavity above the septum.

The improved septum configuration of the present invention provides a substantial improvement in septum life (as measured by average number of penetrations before leakage) especially when silicone based elastomers are used.

The principal problem in maintenance of septum life is caused by loss of material through coring, tearing or abrasion on the sides of the septum opening. Needles with rounded ends and holes in the side thereof, as disclosed in copending application Ser. No. 138,579, substantially minimize coring problems. However, there remains some possibility of paring the septum material as the needle is inserted or removed along the side of the needle passage. The present design substantially lessens this problem by providing additional room for material displacement when the needle is inserted through the septum. By providing room for septum material displacement, the septum does not undergo as much compression when the needle is inserted and consequently there is less tendency for septum material to push into the needle opening as the needle passes through the septum.

The preferred embodiment of the septum configuration is shown in FIGS. 4-6. The precut needle openings are two slits 21 cut through the septum and extending from near the center of the septum out to the edge thereof. For a septum of about 0.44 inches between ends 19, the uncut center portion 30 is only about 0.04 inches wide.

The edges of the septum have a groove 32 therein encircling the entire body thereof. Groove 32 carries an elastomeric ring 34 which preferably has an elliptical or circular cross-section. Ring 34 which has a smaller inner circumference than that of the septum serves to hold the slit septum together and maintain the slit surfaces together in sealed relationship by applying an inwardly directed radial force on the septum. The elliptical or circular shape of the ring leaves gaps in the groove into which septum material may move as the needle is inserted.

The septum is also preferably provided with an elongated bottom recess 36 and a pair of generally semi-spherical top recesses 38 aligned with holes 23 in pressure plate 22 when assembled in the blood access device stem.

Functionally, the septum configuration shown in FIGS. 4-6 operates in two modes. When the needles are not inserted into the septum, the septum operates under a compression mode hermetically sealing the blood conduit by coacting with support member 15 and pressure plate 22. Elastomeric ring 34 provides radial compression to hermetically close the septum openings created by slits 21. When a needle or needles are inserted through the septum slits, the outwardly expanding septum material is accommodated by the space provided in groove 32 while the downwardly expanding septum material is accommodated by recess 36. The radial force exerted by the elastomeric ring 34 seals the needle or needles between the blood stream and the cavity of stem 11. The radial force exerted by ring 34 thus causes the septum to operate in a shear mode. Because the present septum operates in both a compression and a shear mode, substantial increases in the working life of an elastomeric material such as the preferred silicone based elastomers are achieved.

The material displacement characteristics of the new septum are illustrated in FIG. 7. Comparison of this Figure in which the needles have been inserted through the septum with the relaxed septum shown in FIG. 3 shows that the gaps in groove 32 have been substantially filled and the bottom recess partially filled by displaced septum material. It should also be noted that, as the needles are inserted, septum material parts along the slit so that, when the needles have side openings aligned with the slit as shown in FIG. 7, there is a reduced tendency for septum material to press inwardly on the needle openings and become pared thereby.

Whereas the preferred embodiment of the septum of the present invention has a pair of oppositely directed slits through the septum extending all the way to the edges thereof, other slit configurations may be employed without departing from the essence of the invention if such embodiments employ a circumferential side groove carrying an elastomeric compression ring therein as disclosed in the present application. Specifically, it is contemplated that alternative embodiments may employ oppositely directed slits which do not extend all the way to the edges of the septum or a single central slit which likewise does not extend all the way to the edges of the septum.

It has also been found that, after insertion of the septum into the stem 11 of device 10, the slits 21 are initially resistant to penetration by a needle. It is therefore preferable that the initial penetration of the septum within the device be made by an obturator as shown in FIG. 1a. The obturator has a body 130 which may be inserted into the cavity in stem 11, a pair of blank needles 132 which have rounded bottoms and no holes therethrough extending downwardly from body 130 and having the same spacing as that of a needle carrier structure disclosed hereafter, and a finger hold 134 to facilitate insertion of the device into the septum or removal therefrom. After one or two penetrations by the obturator, the septum is much less resistant to penetration by a needle and therefore needles having holes in the sides thereof may be inserted repeatedly with a reduced likelihood of paring or coring the slit surfaces.

Improved Cap Structure

The improved cap member 40 snaps over flanged edge 42 of the blood access device stem. The cap member is held in sealed relationship therewith without the need for a retaining ring. This is accomplished by making the cap from a flexible material and by providing the interior side surface of the cap with a groove 44, the diameter of which is slightly smaller than that of the outer diameter of flanged edge 42 with which the cap surface engages. It is necessary that the cap be made of a flexible material so that it may be snapped over the slightly larger flange 42. The cap also has a downwardly projecting central portion 47 which fits into the cavity of stem 11 for alignment purposes.

The outer projecting surface 46 is flared downwardly in a cone shaped manner, the lower flared edge 49 being spaced when in use slightly above the skin layer 50 of the user. Pressure contact between edge 49 and the skin is undesirable as necrosis may occur. The flared contour of cap 40 is desirable, however, because it provides a profile for the exposed external portion of member 10 that is less likely to catch an object such as clothing. To reduce pressure applied by the cap if it occasionally comes in contact with the skin, the flared exterior surface 46 of cap 40 is provided with a plurality of slits 52 which increase the flexibility of the exterior surface 46. The slits 52 also provide increased air circulation under the cap thereby aiding in preventing infectious growth on the skin around the protruding stem of member 10.

Improved Needle Assembly

The improved needle assembly is illustrated in FIGS. 1, 7 and 9. The needle carrier 52 includes parallel right angle tubing connectors 54 which provide the structure with an improved profile, allowing easy insertion of the needles into the device by thumb pressure and eliminating the awkwardness of tubing 55 coming in from different directions as was the case with the needle carrier structure of application Ser. No. 138,579. Maintaining the tubing pair in closely spaced parallel relationship and at right angles to the needle carrier lessens the dangers of entanglement and consequential damage to the implant or disconnection of the blood flow.

It is desirable, however, to have the needles more closely spaced together than is typically possible to space the tubing. The further the needles are spaced apart, the larger implanted member 10 must be. The improved needle carrier therefore contains internal channeling which allows for closer spacing of the needles than of the connected tubing.

Member 52 is most conveniently manufactured as a multi-part structure. The basic element of the needle carrier is body member 58 which has lower apertures 60 into which needles 62 may be adhesively or otherwise secured. A circular flange 64 provides an attachment surface for a-clip not shown to fasten the needle assembly to the flange 42 on stem 11. Male fittings 68 extend above flange 64. Female openings on hollow right angle tubing connectors 54 engage members 68. The centers of needles 62 are spaced closer together than those of tubing connectors 54 and male members 68 by providing members 68 with a tapered non-concentric bore 70 as is best shown in FIG. 7. This bore channels the blood flow between the needles and the further spaced apart tubing connectors 54.

To assure proper orientation of the needles with the slits in septum 18, the tubing connector body 58 may be provided with protrusions not shown which conform to the internal shape of the opening in stem 11 as shown in FIG. 2.

The needles of the improved assembly preferably have two or more small side holes 78, one above the other, rather than a single large hole. This structure maintains flow while minimizing needle hole contact with the septum slit surfaces.

Unless the needles are made of a self-lubricating material, the needles must be provided with a surface lubricant such as a silicone fluid or oil to reduce abrasion as the needles pass through the septum.

Septum Assembly Loading Tool

The preferred form of the septum assembly loading tool is shown in FIGS. 10-13. The basic elements of the tool are the hollow outer body member 80 and a plunger member 81 within and extending upwardly out of body member 80. Twin pins 82 attached to the lower surface of plunger member 81 extend downwardly through the lower opening in body member 80. For ease of manufacturing, body member 80 is made of two separate portions 83 and 84. Likewise, plunger member 81 is made of two parts, lower member 85 and upper xember 86.

Member 84 has a stem insertion portion 87, the diameter of which, as can be best seen in FIG. 13, is slightly less than the blood access device stem opening above ring retaining ridge 88, but greater than that of the retaining ridge. Therefore, when the loading tool is inserted into the stem, the lower surface 89 of member 80 rests against ring retaining ridge 88.

At least the lower portion 90 of the bottom opening into body member 80 has a diameter slightly less than that of retaining ridge 88. When loaded, a crimped retaining ring 24 is held within body member 80 by inner opening surfaces 90. In the preferred embodiment, a shoulder 91 on the inner portion of member 80, against which the outer portion of the upper side of retaining ring 24 may rest, is provided.

The cross-section of the lower surface 92 of plunger member 81 is of sufficient width so that surface 92 engages at least a portion of the upper side surface of retaining ring 24 when the plunger is depressed. This engagement is shown in FIG. 13.

Pins 82 carry the pressure plate 22 and the septum 18, holding them in proper alignment for insertion. As shown in FIG. 13, when the plunger is depressed, the septum, pressure plate and retaining ring are pushed downward until the retaining ring snaps into the retaining ring groove 96 under ridge 88. This requires some compression of the septum 18, as shown in FIG. 13.

The plunger is held in the withdrawn position by means of rod 98 which passes through hole 99 in the plunger above the upper surface of body member 80. Rod 98 engages the upper surface of body member 80 and serves as a stop means for the plunger. Withdrawal of rod 98 permits the plunger to be depressed.

Stem Clamping Forceps

FIGS. 14-18 depict a stem clamping forceps 100 which is designed to be used with implanted blood access device 10. The body of the clamp is a standard forceps clamp having opposing arms 101 and 102. The ends of the clamp, however, are specially adapted to engage upper stem flange 42 of device 10. This is accomplished by providing the ends of arms 101 and 102 with semi-circular interior opening surfaces 103 and 104, respectively, which are sized to fit about the outer diameter of stem 11. Central grooves 105 and 106 securely engage flange 42 of stem 11 as shown in FIG. 15.

The ends of the clamp are also provided with oppositely disposed finger holds 108 which project upwardly and curve outwardly from the ends of the clamp. As shown in FIG. 18, these ear-like finger holds are used to hold stem 11 against downward pressure which may be exerted on device 10, as for instance, when the thumb is used to depress the plunger of the septum loading tool as disclosed herein. The stem clamping forceps may also be useful for holding the blood access device in place during surgical implantation thereof.

In the preferred form of the forceps clamp of this invention, arms 101 and 102 have a flattened S-shaped curve thereon as is shown in FIGS. 16 and 18. This shape allows the clamp to be more easily manipulated since the ends of the clamp are held closely against the skin of the implant recipient.

Back-up Septum System

The back-up septum clamp is a device by which a spacer member and a circular septum may be held within the opening in stem 11 of device 10 above the retaining ring 24 in such a manner that the circular septum seals against the interior surfaces of stem 11, thereby stopping leakage of blood occurring because the principal septum has begun to leak.

The back-up septum clamp has three principal parts. Semi-circular members 110 and 111 having interior grooves 112 and 113, respectively, sized to engage flange 42 of stem 11, are held together by means of screws 114.

Within the cavity of stem 11, there is placed a spacer member 138 which has an outer ring 140 and a depressed central portion 142. Spacer member 138 defines two holes 144 through which a needle pair may pass. Member 138 sits above retaining ring 24, outer ring 140 providing an unbroken circumferential surface against which the lower edge of a back-up septum 118 may be compressed.

Generally, circular elastomeric septum member 118 is placed within the opening in stem 11 above the spacer ring 138. The septum is held in place by clamp cap member 120. Cap member 120 has a central aperture 121 and a circular downwardly projecting portion 122 which fits into the opening in stem 11. Cap member 120 is held in place by means of screws 123 which pass through holes 125 in the cap member and engage holes 126 and 127 in members 111 and 110, respectively. As screws 123 are tightened downward, central portion 121 pushes against septum 118 causing it to bulge outwardly. The outward bulging of septum 118 seals the septum against the inner surfaces of the cavity in stem 11 and against spacer 138, effecting closure of the stem until assistance in replacing the leaking principal septum can be obtained.

If septum 118 is provided with precut holes or slits aligned with slits 21 in the primary septum and holes 23 and 144 in the pressure plate 22 and spacer member 138, respectively, continued access may be provided to the circulatory system while the back-up septum is in place. In such case, the depressed portion 142 of spacer member 138 allows septum 118 to function in the form of a floating diaphragm. This permits the septum to flex as the needles are inserted or removed, thereby facilitating insertion and removal of a needle or needles into the blood access device and reducing friction or abrasion of the back-up septum caused by passage of the needle therethrough. The configuration of spacer member 138, including a central portion 142, is preferred over a simple ring having the configuration of outer ring 140 because central portion 142, while providing some space for septum 118 to flex downwardly, substantially fills the dead space between pressure plate 22 and back-up septum 118, thereby reducing the volume in which blood leaking through the principal septum 18 may collect.

Implant Cap

Implantation of the blood access device of copending application Ser. No. 138,579 is preferably accomplished by cutting a first opening through the skin into the body, connecting the device to the circulatory system, tunneling under the skin to a second opening through the skin and pulling the device through the tunnel by means of suture material wound about the body of the device so that stem 11 is pulled up through the second skin opening. To accomplish this without filling the cavity in stem 11 with tissue or blood, device 10 is preferably provided with a hemispherical cap 150 shown in FIG. 23 and in phantom in FIG. 3 which is used to cover stem 11 during implantation.

Cap 150 is a generally hemispherical member having a lower protrusion 152 which fits into the cavity of stem 11. Number 150 also has a tab 154 on the top thereof defining an opening 156 through which suture material 158 wrapped about device 10 may be passed. The winding of the suture material as shown in FIG. 23 permits a surgeon to pull the device 10 into place in the second skin opening as described in the previous paragraph.

Alternate Back-up Septum System

Figure 24:
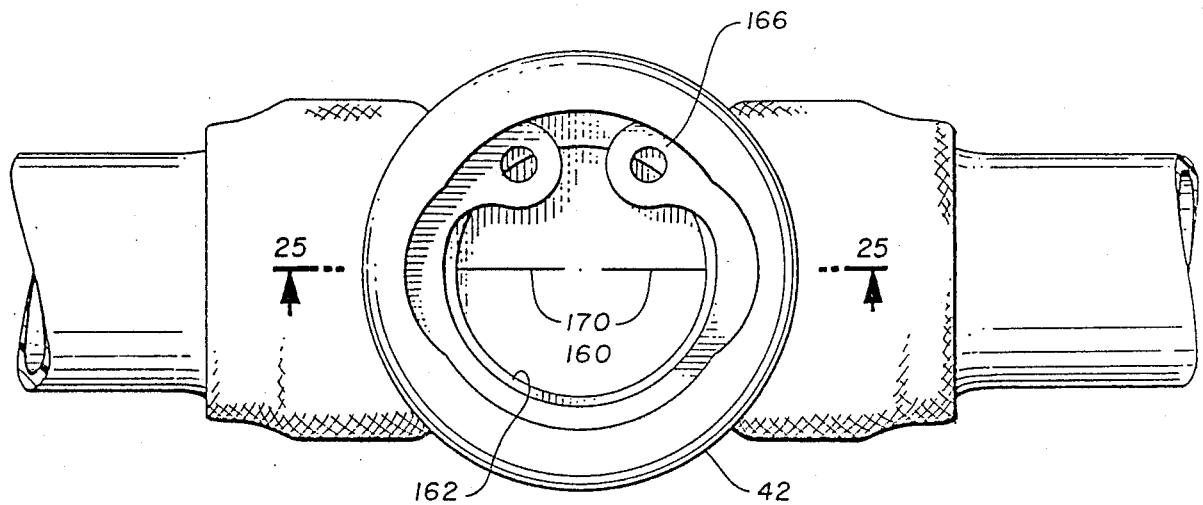
FIG. 24 is a top plan view of the assembly of FIG. 2.

FIG. 24 is a top plan view of the implantable T-shaped assembly as in FIG. 2, but with the back-up septum held in place above the principal septum by means of a retaining ring as disclosed hereinafter.

Figure 25:
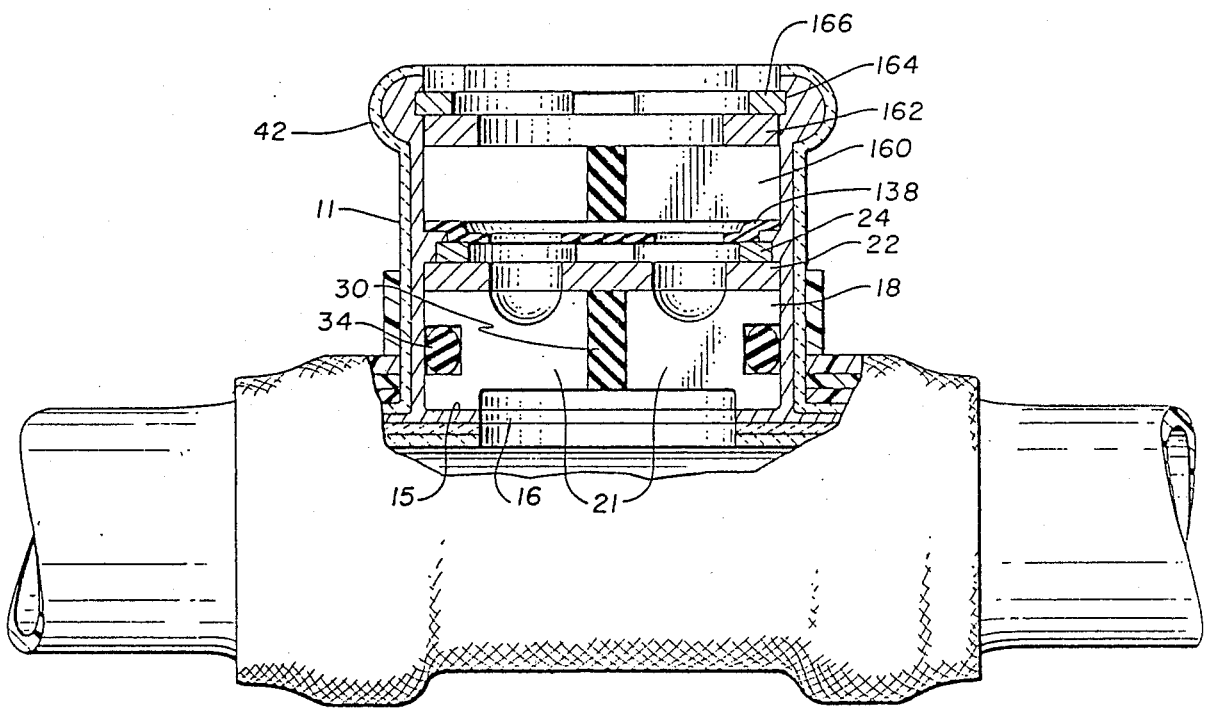
FIG. 25 is a side elevational view taken along lines 25—25 of FIG. 24.

FIG. 25 is a side elevational view partly in section as taken along lines 25—25 of FIG. 24.

As an alternate to the back-up septum clamp as described hereinbefore, a back-up septum 160 may be held within the stem cavity of device 10 by means of a compression ring 162 and a retaining ring 166. To do so, the upper portion of the cavity in stem 11 is provided with a groove 164 in which a retaining ring similar to but slightly larger than ring 24 may be held. The backup septum system of this alternative embodiment also employs the spacer 138 which is shown in FIGS. 21 and 22.

The compression ring 162 conforms generally to the shape of the T-stem cavity and has a thickness such that, when retaining ring 166 is in place, the compression ring exerts sufficient pressure on septum 160 to cause the septum to seal the cavity opening.

By providing septum 160 with openings therethrough such as slits 170, continued access to the circulatory system can be achieved.

Septum 160 may, but need not, have a side groove carrying an elastomeric ring similar to the construction of improved septum 18.

What is claimed is:

1. An improved elastomeric septum closure for use with an implantable blood access device having a body external opening thereto, the septum having a top surface, a bottom surface and a circumferential side surface, the improvement comprising a circumferential groove in the side surface, an elastomeric ring within the groove, said ring having an interior diameter at rest less than that of said groove, and at least one elongated slit through the septum from the top surface to the bottom surface whereby a needle or other cannulae may be passed through the septum.

2. A septum as in claim 1 wherein said septum has an elongated central recess in the bottom thereof extending at least part way along said slit.

3. The septum of claim 2 further having at least one semi-spherical recess in the top thereof aligned with said slit defining an entry point for said needle.

4. A septum as in claim 1 wherein said ring has an elliptical cross section.

5. The septum of claim 1 wherein said ring has a circular cross section.

6. The septum as in claim 1 wherein said septum has a generally oval shape.

7. The septum of claim 1 made of a silicone based elastomer.

8. A septum as in claim 1 having two oppositely directed said slits therethrough extending from near the center thereof to the edge thereof, an elongated central recess in the bottom thereof extending between and part way along said slits, a pair semi-spherical recesses in the top thereof, one centered on each said slit, said top recesses defining entry points for a needle pair, and wherein said ring has an elliptical cross section.

* * * * *